United States Patent
Aita et al.

(10) Patent No.: US 9,598,505 B2
(45) Date of Patent: Mar. 21, 2017

(54) SILYL-DERIVATIVES OF POLYSACCHARIDES

(75) Inventors: Gaspare Aita, Settimo Milanese (IT); Demetrio Manenti, Milan (IT); Pasqualino Rossi, Rome (IT); Giuseppe Rosano, London (GB)

(73) Assignee: SILDEHA SIXASS S.A., Paradiso (CH)

( * ) Notice: Subject to any disclaimer, the term of this patent is extended or adjusted under 35 U.S.C. 154(b) by 788 days.

(21) Appl. No.: 13/582,750

(22) PCT Filed: Mar. 4, 2011

(86) PCT No.: PCT/IB2011/000455
§ 371 (c)(1),
(2), (4) Date: Sep. 28, 2012

(87) PCT Pub. No.: WO2011/107866
PCT Pub. Date: Sep. 9, 2011

(65) Prior Publication Data
US 2013/0029934 A1     Jan. 31, 2013

(30) Foreign Application Priority Data
Mar. 5, 2010   (IT) .............................. MI2010A0365

(51) Int. Cl.
| | | |
|---|---|---|
| *C08B 37/00* | (2006.01) | |
| *C08B 37/08* | (2006.01) | |
| *C08B 37/10* | (2006.01) | |
| *C08B 31/00* | (2006.01) | |
| *A61K 31/728* | (2006.01) | |
| *A61K 31/727* | (2006.01) | |
| *A61K 31/722* | (2006.01) | |
| *A61K 31/726* | (2006.01) | |
| *A61K 31/718* | (2006.01) | |
| *A61K 8/73* | (2006.01) | |
| *C08L 5/08* | (2006.01) | |
| *C08L 5/10* | (2006.01) | |
| *A61Q 19/06* | (2006.01) | |
| *A61Q 19/08* | (2006.01) | |

(52) U.S. Cl.
CPC ............ *C08B 37/0072* (2013.01); *A61K 8/73* (2013.01); *A61Q 19/06* (2013.01); *A61Q 19/08* (2013.01); *C08B 37/00* (2013.01); *C08B 37/0063* (2013.01); *C08B 37/0075* (2013.01); *C08L 5/08* (2013.01); *C08L 5/10* (2013.01)

(58) Field of Classification Search
CPC ...... A61K 8/73; C08B 37/00; C08B 37/0063; C08B 37/0072; C08B 37/0075; C08L 5/08; C08L 5/10; A61Q 19/06
USPC ... 514/55, 60, 56, 54; 536/102, 20, 21, 55.1, 536/123.1
See application file for complete search history.

(56) References Cited

U.S. PATENT DOCUMENTS

| | | | |
|---|---|---|---|
| 6,140,481 A | 10/2000 | Hara et al. | |
| 7,662,800 B2 * | 2/2010 | Manenti et al. | ................. 514/54 |
| 2002/0058763 A1 | 5/2002 | Duval | |
| 2002/0115836 A1 | 8/2002 | Tsang et al. | |
| 2008/0318022 A1 | 12/2008 | James et al. | |

FOREIGN PATENT DOCUMENTS

| | | |
|---|---|---|
| EP | 0 385 396 | 9/1990 |
| WO | WO 88/02389 | 4/1988 |
| WO | WO 2004/013182 | 2/2004 |
| WO | WO 2005/028632 | 3/2005 |

OTHER PUBLICATIONS

Rénarsson et al. (Carbohydrate Research 343 (2008) 2576-2582).*
Nishizawa, E.E. et al., "Preparation and Anti Coagulant Activity of Tri Methyl Silyl Heparin in Carbowax", Journal of Medicinal Chemistry, vol. 18, No. 3, (1975), pp. 250-253.
International Search Report for PCT/IB2011/000455, mailed Oct. 24, 2011.
Written Opinion of the International Searching Authority for PCT/IB2011/000455, mailed Oct. 24, 2011.
Italian Search Report for IT Application MI20100365, dated Sep. 24, 2010.

* cited by examiner

*Primary Examiner* — Jonathan S. Lau
*Assistant Examiner* — Michael C Henry

(57) ABSTRACT

The present invention relates to novel silyl-derivatives of polysaccharides and their salts, the processes for their preparation and their use in cosmetic/pharmaceutical field.

5 Claims, 5 Drawing Sheets

SILYL-DERIVATIVES OF POLYSACCHARIDES

This application is the U.S. national phase of International Application No. PCT/IB2011/000455, filed 4 Mar. 2011, which designated the U.S. and claims priority to Italy Application No. MI2010A000365, filed 5 Mar. 2010, the entire contents of each of which are hereby incorporated by reference.

FIELD OF THE INVENTION

The present invention relates to novel silyl-derivatives of polysaccharides and their salts, the processes for their preparation and their use in the cosmetic/pharmaceutical field.

PRIOR ART

Polysaccharides are polymer compounds formed by repeating base units of mono- or disaccharides joined by glycosidic bonds. These compounds are often heterogenic and contain repeating units that are slightly modified with respect to one another and with respect to the base unit. These are nonetheless macromolecules which, according to their structure, can have characteristics and properties different from those of the respective base units.

Hyaluronic acid (HA) is the main component of a family of polysaccharides better known as Glucosaminoglycans.

Its structure corresponds to that of an unbranched linear polymer composed of a disaccharide unit formed by glucuronic acid and N-acetylglucosamine which is repeated in the molecule a large number of times, until reaching molecular weights in the order of several million Daltons.

The interest for this molecule has increased greatly in recent years, as it is used with wide success in aesthetic surgery to treat wrinkles, in ophthalmic surgery as therapeutic principle in some degenerative arthropathies.

Cosmetic/pharmaceutical use of hyaluronic acid is linked to the chemical characteristic of the molecule to arrange itself according to a "ball of wool" configuration, thereby capable of taking up a very large volume of water. Moreover, the presence of carboxyl groups and hydroxyl groups arranged along its polysaccharide chain give it marked visco-elastic properties and substantial affinity for water.

Due to its ability to absorb and retain large quantities of water, hyaluronic acid is therefore capable of maintaining the right degree of humidity on the skin even in the presence of a very low external humidity level. Hyaluronic acid is also a fundamental component of synovial liquid. This liquid is located inside the joints and its purpose is to protect cartilage from wear and from excessive loads. Besides absorbing movements, synovial liquid nourishes cartilage, accelerating healing processes. Joint aging, just as cutaneous aging, is associated with a decrease in the production of synovial liquid.

Hyaluronic acid is particularly effective in the treatment and prevention of osteoarthritis, a degenerative disease that affects cartilage. Intra articular infiltrations of this substance can in fact reduce pain, and at the same time accelerate healing processes. Therapy based on hyaluronic acid has proved effective above all in lesions of medium and small size.

In this field just as in the field of cosmetics, the action of hyaluronic acid is not lasting and this makes it necessary to repeat the treatment or application every 6-12 months.

Hyaluronic acid is also used in ophthalmic, otologic and ocular surgery and in tissue healing and regeneration processes.

The object of the present invention is to provide novel derivative compounds of polysaccharides that are stable, not easily degradable and which can thus maintain an effective action that is long lasting.

Another object of the present invention is to provide one or more processes for the synthesis of novel derivative compounds of polysaccharides that are easy to produce from an industrial point of view.

Yet another object of the invention is to provide derivatives of polysaccharides, including their salts, which can advantageously be used in the cosmetic and/or pharmaceutical field.

In particular, the object of the present invention is to provide derivatives of polysaccharides, including their salts, which can be used advantageously in the cosmetic and/or pharmaceutical field in the treatment and cure of pressure sores, in the treatment and cure of mucosal diseases, for example oral or of the digestive tract, in the treatment and cure of diseases of the mucosa, for example of the respiratory tract, in the treatment and cure of dermal aging, for example in the case of dermatitides and in anti-aging treatment, in the treatment and cure of panniculopathy (cellulite) or also in the treatment and cure of primary and secondary arthrosis and in the treatment and cure of chondropathies (joint cartilage diseases).

A further object of the invention is to provide cosmetic and/or pharmaceutical compositions, comprising the derivatives of polysaccharides and/or their salts according to the invention, which are effective and remain effective for a long time.

DESCRIPTION OF THE INVENTION

These and other objects and related advantages which will be more apparent from the description below are achieved by a polysaccharide compound derivatized with at least one silicon (Si) atom, i.e. a silyl-derivative of polysaccharide.

In other words, the starting polysaccharide is reacted with at least one silicon derivative compound, obtaining an organic silicon compound in which at least one silicon atom is bonded to the polysaccharide through at least one covalent bond.

According to the present invention, the term "derivative" is intended as a compound in which, with respect to a starting compound, at least one atom has been substituted by another atom or by a group of atoms.

In the case of the present invention, the term silyl-derivative of polysaccharide is therefore intended as a compound (in this case the silyl-derivative of polysaccharide) in which, with respect to the starting compound (in this case the polysaccharide), at least one atom (generally hydrogen) has been substituted by another atom (in this case silicon) or by a group of atoms (in this case reactive derivatives of silicon). Substitution was carried out by breaking and forming bonds of covalent type, i.e. bonds characterized by the sharing of atoms that participate in the bonding of at least one pair of electrons. This reaction is also indicated below with the term "silanization".

Silanization can take place on one or more functional groups (for example hydroxyl, carboxyl, amino, sulfate) present on the repeating unit, on all the repeating units or only on some. Therefore, depending on the reaction conditions, the silanization reaction can be carried out, for example, on one repeating unit every 4 or every 20. Again by way of example, by assuming a general formula of a polysaccharide as POH, where P is the structure of the polysaccharide and OH is at least one hydroxyl group present on the polysaccharide structure, the following general formula (I) can be schematized for the novel silyl-derivatives of polysaccharides according to the invention:

POSiY (I)

where an oxygen atom of the polysaccharide is bonded to the silicon by means of a covalent bond and where Y is the balance of the reactive derivative of silicon, for example alkyl or aryl radical.

Alternatively, and always according to the present invention, by assuming a general formula of a polysaccharide as PNH, where P is the structure of the polysaccharide and NH is at least one amino or amide group that may be present on the polysaccharide structure, the following general formula (I') can be schematized for the novel silyl-derivatives of polysaccharides according to the invention:

PNSiY (I')

where a nitrogen atom of the polysaccharide is bonded to the silicon by means of a covalent bond and where Y is the balance of the reactive derivative of silicon, for example alkyl or aryl radical.

For example, a compound can be used as reactive derivative of silicon, selected from: (alkyl and/or aryl) halogen silanes, (alkyl and/or aryl) silanes, (alkyl and/or aryl) silanols, silazanes, disilazanes and other silyls, which reacts with the active hydrogens of the hydroxyl or carboxyl groups, of the acid functional groups of elements different from carbon, of amino and amide groups optionally present in the polysaccharide structure (POH), giving rise to a silyl-derivative of polysaccharide according to the following scheme:

$$\text{Cl}-\underset{\underset{\text{CH}_3}{|}}{\overset{\overset{\text{CH}_3}{|}}{\text{Si}}}-\text{Cl} + 2\text{POH} \longrightarrow \text{PO}-\underset{\underset{\text{CH}_3}{|}}{\overset{\overset{\text{CH}_3}{|}}{\text{Si}}}-\text{OP} + 2\text{HCl}$$

In the example shown above, a dichlorosilane (reactive derivative of silicon) reacts with —OH hydroxyl and carboxyl groups of a polysaccharide (or of two adjacent polysaccharides). Alternatively, the same reaction can also occur with amine and amide —NH$_2$ groups optionally present in the starting polysaccharide, which in this case could conveniently be indicated as POHNH$_2$.

The scheme below instead shows the case in which the reactive derivative of silicon is hexamethyldisilazane, which reacts with the —OH hydroxyl and carboxyl groups of a polysaccharide (or of 2 adjacent polysaccharides), generally indicated as POH.

$$\begin{array}{c}\text{CH}_3\;\text{CH}_3\\ \diagdown\!/\\ \text{Si}\\ \text{CH}_3\diagup\quad\diagdown\text{NH}\\ \text{CH}_3\diagdown\quad\diagup\\ \text{Si}\\ \diagup\!\diagdown\\ \text{CH}_3\;\text{CH}_3\end{array} + 2\text{POH} \longrightarrow 2\text{PO}-\text{Si}-(\text{CH}_3)_3 + \text{NH}_3$$

Also in this case, the same reaction can occur with amine and amide —NH$_2$ groups that may be present in the starting polysaccharide, which could therefore conveniently be indicated as POHNH$_2$.

Therefore, according to the present invention, said reactive derivative of silicon can be indicated by means of one or more of the following general formulae from a) to e) and selected from the following compounds:

a) in the case of halogen silanes:

$$R_nSiX_{4-n}$$

where n is between 0 and 3
R is selected from H, alkyl, aryl, heteroaromatic group, also different from one another
X is halogen b) in the case of silanes:

$$H_nSiR_{4-n}$$

where
n is between 1 and 3
R is selected from alkyl, aryl, heteroaromatic group, also different from one another
H is hydrogen c) in the case of silanols and their ethers:

$$R_nSi(OR')_{4-n}$$

where
n is between 0 and 3
R is selected from H, alkyl, aryl, heteroaromatic group, also different from one another
R' is selected from hydrogen, alkyl, aryl, heteroaromatic group, d) in the case of silazanes:

$$R_3SiNR'$$

where
R is selected from alkyl, aryl, heteroaromatic group, also different from one another
R' is selected from hydrogen, alkyl, aryl, heteroaromatic group, e) in the case of disilazanes:

$$R_6Si_2NR'$$

where
R is selected from alkyl, aryl, heteroaromatic group, also different from one another
R' is selected from hydrogen, alkyl, aryl, heteroaromatic group.

In particular, the subject-matter of the present invention is constituted by the novel silyl-derivatives of polysaccharides, where said polysaccharides are preferably selected from amides, glycosaminoglycans, heparins and hyaluronic acid, hyaluronic acid (HA) being particularly preferred.

By way of example, the reaction between hyaluronic acid and three trimethylchlorosilane molecules in the quality of reactive derivative of silicon according to the aforesaid general formula a) is indicated below. The reactive derivative of silicon reacts with the three types of active hydrogen present on the hyaluronic acid, i.e. hydroxyl, amide and carboxyl hydrogen.

[Chemical structure of hyaluronic acid repeating unit] + 3n Cl—Si(CH$_3$)$_3$

↓

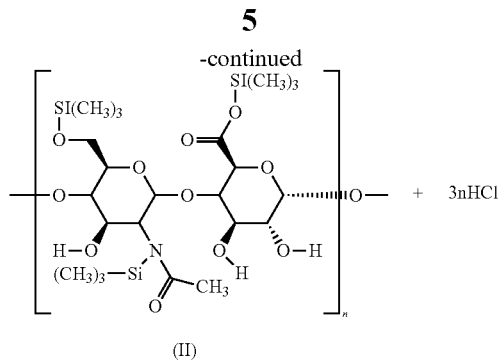

(II)

In the example shown above, the silyl-derivative of polysaccharide according to the present invention will therefore be the compound (II) which is represented by a repeating unit of hyaluronic acid, derivatized with silicon, giving rise to a derivatized polysaccharide compound with at least one silicon (Si) atom.

Again in the case of hyaluronic acid, but in general in the case of suitable polysaccharides, the use of a reactive compound of silicon in the form of halogen silane will give rise to a silyl-derivative that may undergo cross-linking phenomena between two adjacent chains and/or between two points of the same chain, as shown in FIG. 1, which illustrates a structure of a silyl-derivative of hyaluronic acid obtained through the use of a dichlorosilane.

This further cross-linking characteristic further supports the characteristic of the hyaluronic acid molecule to arrange itself according to a "ball of wool" configuration. Therefore, in these conditions the cross-linked silyl-derivative of hyaluronic acid is able to take up even greater volumes of water with respect to its corresponding non cross-linked silyl-derivative. Consequently, this translates into improved activity and greater stability.

In fact, polysaccharides in general and hyaluronic acid in particular are susceptible to enzyme attack with consequent degradation and destruction of the molecule. In particular, hyaluronic acid undergoes attack by the enzyme hyaluronidase according to a diagram that can be simplified as follows:

The hyaluronic acid chain is broken and a double bond is formed.

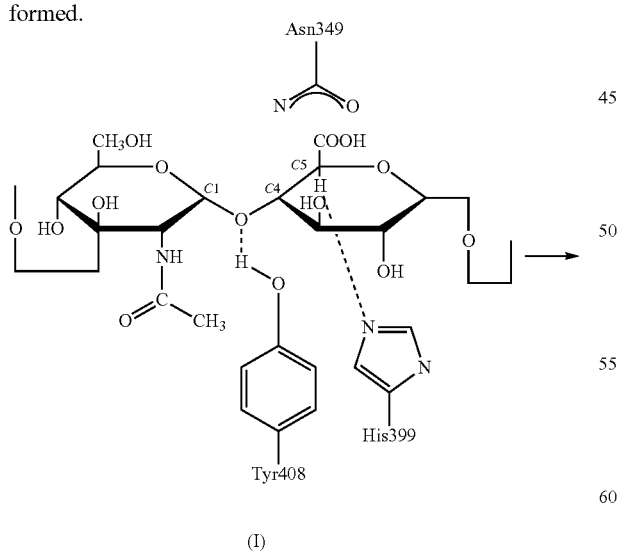

(I)

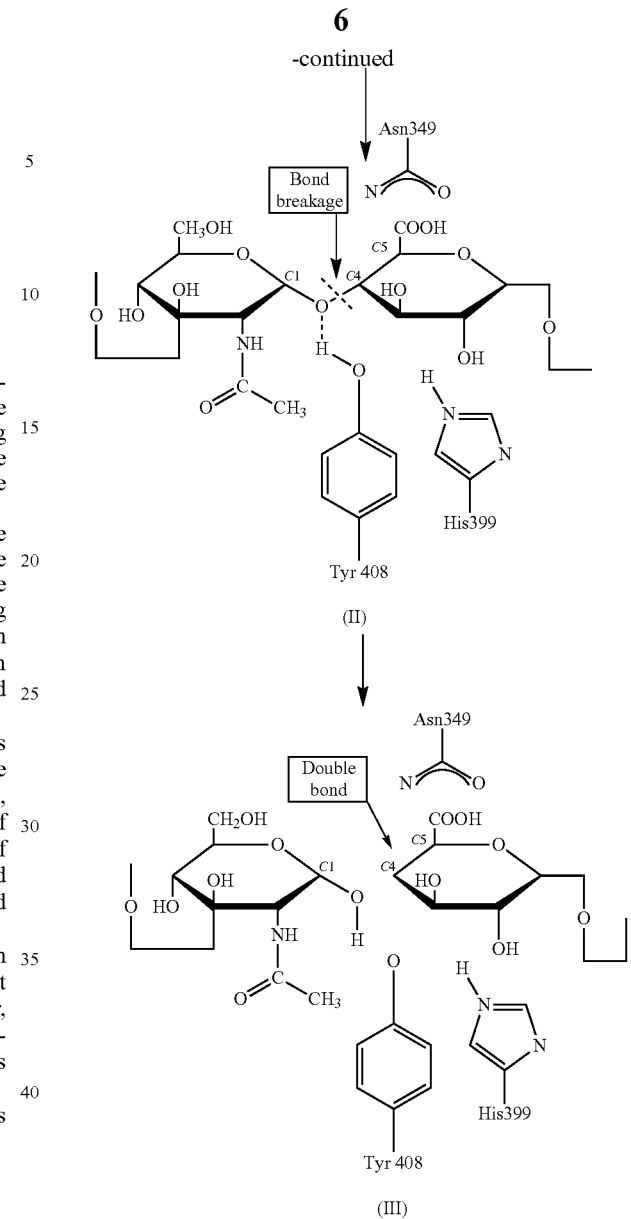

(II)

(III)

Attack by the enzyme hyaluronidase, which interacts with the carboxyl groups of hyaluronic acid, therefore causes breakage of the molecule.

If the same carboxyl groups are at least partly derivatized and modified to give a silyl-derivative, the enzyme hyaluronidase is no long able to interact with them and therefore is unable to perform its degrading action and to cause breakage of the molecule. As a result, the hyaluronic acid remains intact and can perform its action for a longer period of time, as it is no longer subjected to enzymatic degradation.

In the same way, in general polysaccharides tend to be easily susceptible to enzymatic attack and consequent degradation into secondary products. Therefore, also in this case their corresponding silyl-derivatives are "protected" compounds and, not being subjected to enzymatic attack and consequent degradation, their characteristics remain unchanged for a longer period of time.

The corresponding silyl-derivatives of chitosan, in which a silyl group was bonded to the oxygen of the hydroxyl and/or to the nitrogen of the amine group, are characterized by modified chemical-physical properties and biological activities.

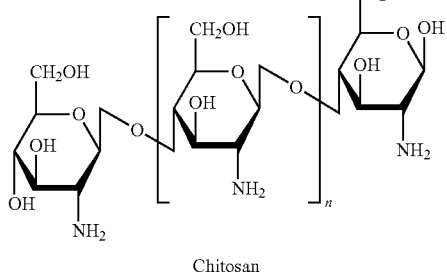

Chitosan

In the case of heparins, compounds of the family of glycosaminoglycans widely used as injectable anticoagulants, the corresponding silyl-derivatives in which silicon has substituted some functional groups of the heparins are characterized by modified chemical-physical properties and biological activities.

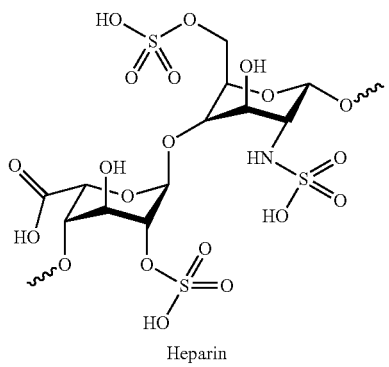

Heparin

By way of example, the diagram relating to preparation of the corresponding silyl-derivative of heparin is shown below.

In this case, the reactive derivative of silicon, i.e. trimethylchlorosilane, reacts with a sulfate group present on the heparin.

On the basis of the used molar ratio and of the reaction conditions, the reaction can occur on some repeating units present in the polymer chain.

The reaction preferably takes place on the group containing the most active (acid) hydrogen and located in a position with least steric hindrance.

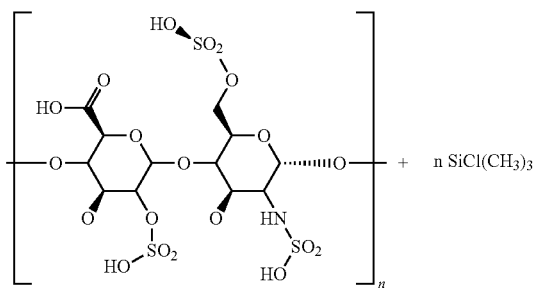

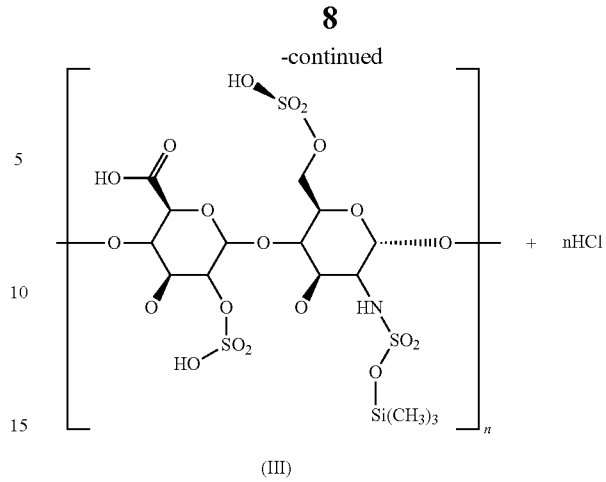

(III)

According to the present invention, the process for the preparation of silyl-derivatives of polysaccharides provides that the reaction between said polysaccharides and said reactive derivatives of silicon, for example silanes, takes place in an anhydrous medium in heterogeneous phase, for example in liquid-solid or gas-solid phase.

The reaction is conducted in such a manner that silanization, i.e. substitution of at least one functional group with at least one silicon atom, of all the available groups of the polysaccharide, is not carried out, to prevent excessive modification of the properties of the starting molecule.

In practice, with the process according to the invention, it is possible to obtain a silyl-derivative of polysaccharide characterized in that silanization, i.e. derivatization with at least one Silicon atom, occurs only on part of the available functional groups (hydroxyl, carboxyl, amine, sulfate) of the repeating unit, on all the repeating units or only on some.

The silyl-derivatives according to the present invention exhibit greater resistance to enzymatic destruction with respect to the starting polysaccharide and significant modifications of the chemical-physical characteristics.

Figure 1:
FIG. 1 illustrates a silyl-derivative of hyaluronic acid obtained through the use of a dichlorosilane.

The variation in the polysaccharides/silicon derivatives weight ratio makes it possible to obtain a noteworthy variety of products with different degree of silanization.

It has surprisingly been observed that the "silanization" reaction modifies many chemical-physical properties of the silyl-derivatives according to the present invention, for example it greatly decreases the viscosity, lowers the radius of gyration of the polymer and therefore its spatial structure, increases the resistance to enzymatic destruction, modifies the water relaxation times, and therefore the resulting silanized derivative has liquid-like behaviour, in contrast to native solid-like behaviour.

It has also been observed that these structural modifications due to the "silanization" reaction also cause consequent modifications of the biological activity of the compounds.

In order to highlight the differences between the starting polysaccharide compound and its silanized derivative or silyl-derivative according to the present invention, the significant difference in dynamic viscosity encountered for the sodium hyaluronate (sodium salt of the polysaccharide, also indicated as HA Na) and its corresponding silyl-derivative according to the invention is shown below.

The dynamic viscosity of the solutions in water at 0.5% of the sodium hyaluronate is equal to 22.8 cp, while the dynamic viscosity of the corresponding silyl derivative according to the present invention is equal to 1.69 cp.

Likewise, the following graphs are attached to show, in relation to a series of parameters used typically to evaluate the chemical-physical characteristics of polymers, the different properties, and consequently the different characteristics, that distinguish polysaccharides and their salts from the corresponding silanized derivatives or silyl-derivatives thereof according to the present invention.

| RADIUS OF GYRATION | |
|---|---|
| HA Na | 134 nm |
| Silyl derivative | 74 nm |

The water relaxation times, indicated as T1 and T2, indicate a greater mobility of the water in the silyl derivative according to the present invention (Silyl HA), compared to non-silanized hyaluronic acid sodium salt (HA Na). The silanized derivative according to the invention therefore has liquid-like behaviour (i.e. behaviour similar to that of a compound in liquid state), while the starting polysaccharide has a solid-like behaviour (i.e. behaviour similar to that of a compound in solid state).

| RELAXATION TIME | | | |
|---|---|---|---|
| HA Na | T1 3200 | T2 970 | T1/T2 3,3 |
| Silyl HA | T1 2800 | T2 1550 | T1/T2 1,8 |

Synthesis Reactions

The heterogeneous liquid-solid reaction is carried out using liquids having the characteristic of not being solvents for silicon derivatives and for polysaccharides, while having the characteristic of being solvents of the silanizing agent, which have no active hydrogens and are chemically inert against the reagents (silicon derivatives, polysaccharides and silanizing agents) and the reaction products.

For this purpose, aliphatic, aromatic and heteroaromatic, also halogenated hydrocarbons can be used, for example selected from: petroleum ether, pentane, hexane, cyclohexane, heptane, octane, isooctane, benzene, toluene, xylene, ethylbenzene, carbon tetrachloride.

To obtain variations on the products obtained, small quantities of compounds with active hydrogens, such as water (generally always present as impurity), ethanol, methanol, amines, amides or acids can be introduced into the reaction system. Always according to the present invention, some examples of reactive derivatives of silicon are compounds selected from:
trimethylchlorosilane
dimethyldichlorosilane
methyltrichlorosilane
triethylchlorosilane
diethyldichlorosilane
ethyltrichlorosilane
trimethylsilanol
dimethylsilanediol
trimethylsilazane
hexamethyldisilazane
N-Methyl-N-trimethylsilyl-acetamide
N-Methyl-N-trimethylsilyl-trifluoroacetamide
N, O-bis-trimethylsilylacetamide
N, O-bis-trimethylsilyl-trifluoroacetamide
N-trimethylsilyl-diethylamine
N-trimethylsilyl-imidazole.

To shift the reaction equilibrium to the right, i.e. to the advantage of the silanized derivative reaction products of the starting polysaccharides, in order to obtain a product with high silanization, bases without active hydrogens are advantageously used, for example: trimethylamine, triethylamine, pyridine.

With reference to the description above, purely by way of non-limiting example, some examples of reactions for obtaining the silyl-derivatives of polysaccharides according to the present invention are given below.

EXAMPLE 1

Silanization of Hyaluronic Acid 1 g of sodium hyaluronate in fine powder is suspended by stirring in 20 cc of n hexane.

5 ml of n hexane solution containing 1 ml of dichlorodimethylsilane is added slowly. This is kept under stirring for 60 minutes.

It is filtered and the solid is washed on a filter with n hexane until neutral reaction. Alternatively, it can be washed with methanol or with ethanol until neutral pH. Subsequently, the product is vacuum dried at a temperature of 30° C.

The reaction produces a low silanization yield, on average one repeating unit of hyaluronic acid every 20-50 is silanized.

To obtain more effective and complete silanization, the reaction is advantageously conducted under a flow of nitrogen or other dry inert gas, in the presence of a base with no active hydrogens.

The base, for example triethylamine, reacts with the halogenhydric acid produced by silanization with an organohalogen silane.

The triethylammonium formed can partly substitute sodium in salification of the carboxylate group of the hyaluronic acid.

Figure 2:
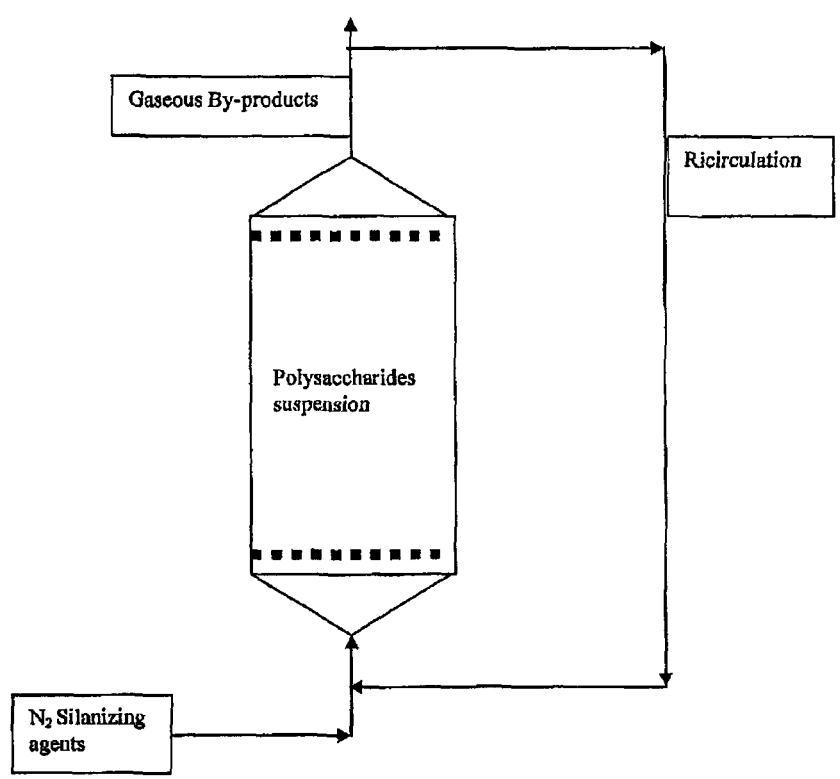
FIG. 2 shows the diagram of a gas-solid reactor suitable to conduct reactions according to the process of the invention.
Figure 3:
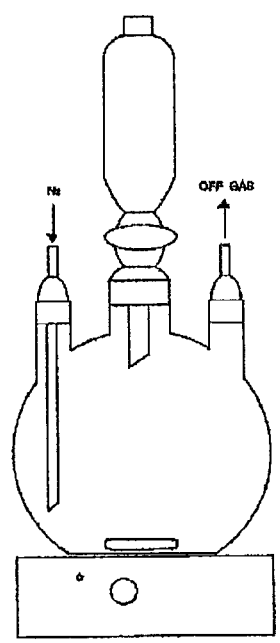
FIG. 3 shows the diagram of a liquid-solid reactor, again suitable to conduct reactions according to the process of the invention.
Figure 4:
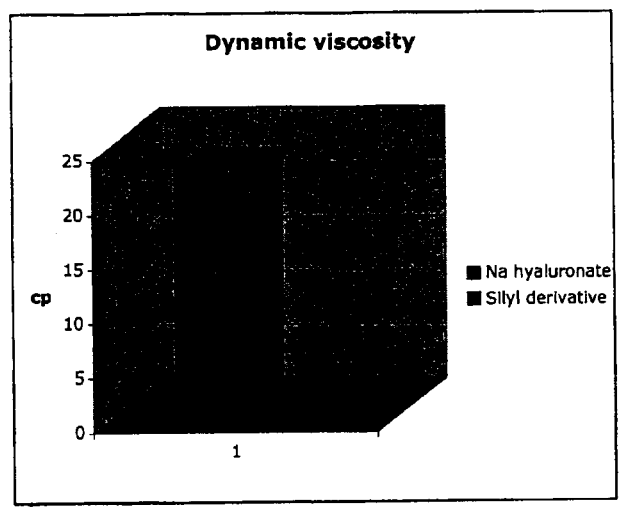
FIG. 4 shows dynamic viscosity for sodium hyaluronate and corresponding silyl-derivative.
Figure 5:
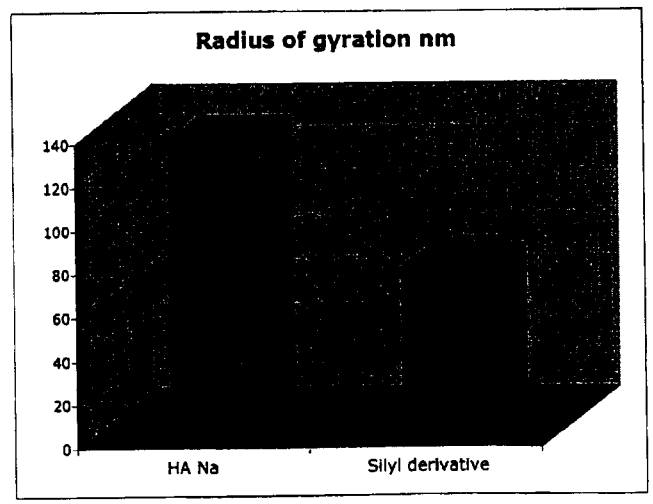
FIG. 5 shows the radius of gyration for sodium hyaluronate and corresponding silyl-derivative.
Figure 6:
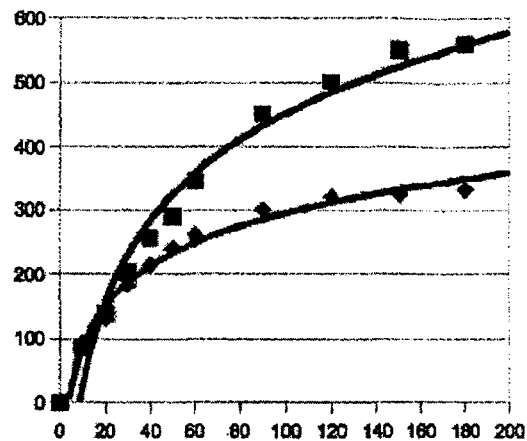
FIG. 6 shows the rate of destruction versus abs (absorbance)/time (in minutes) where the square symbols are Na hyaluronate destruction and the rhombus symbols are silyl-derivative destruction.
Figure 7:
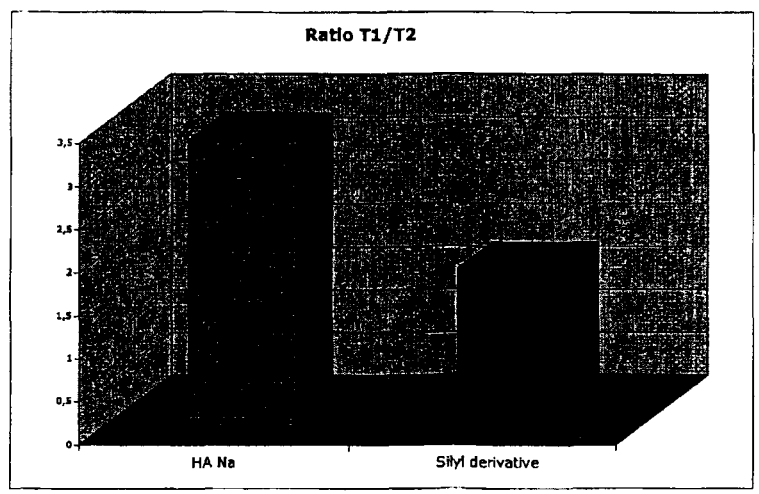
FIG. 7 shows relaxation times for Na hyaluronate and the silyl-derivative.

The new counterion modifies the chemical-physical properties of the derivative both in terms of the greater steric hindrance with respect to sodium and of the interactions with hydrogen bridges. The equipment indicated in FIGS. 1 and 2 is used.

EXAMPLE 2

Silanization of Hyaluronic Acid in the Presence of a Base 4.4 ml of triethylamine is added under stirring to 80 ml of n hexane, followed by 1 g of Na hyaluronate in powder and 2 ml of (CH$_3$)$_2$SiCl$_2$ dissolved in 6 ml of n hexane. This is maintained under stirring for 1 hour, at 30° C. and then vacuum filtered and washed with hexane+1% of triethylamine, a mixture of methanol+10% of triethylamine is poured over the precipitate and maintained in contact for 5 minutes and then it is filtered and washed with hexane.

Subsequently the product is vacuum dried at a temperature of 30° C.

On average, one repeating unit of hyaluronic acid every 4 is silanized. The following reactions occur:

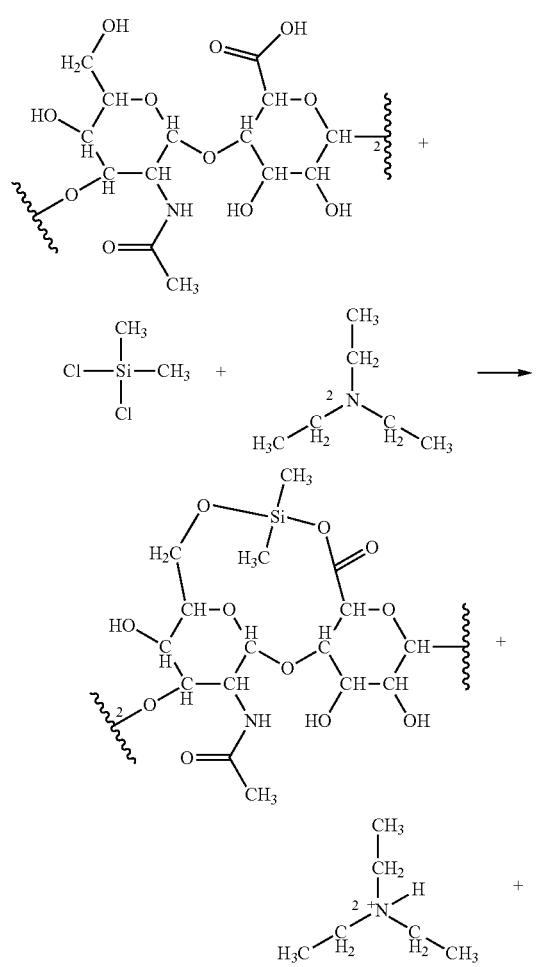

The example shows a silanization reaction of the carboxyl group and of a hydroxyl group of the same repeating unit.

However silanization reaction between 2 groups (hydroxyl and/or carboxyl) of adjacent units or of adjacent chains can also occur.

In this latter case the cross-linked product is obtained.

Again by way of example, other reactions which may occur during the main reaction, when the product is treated with methanol, are shown.

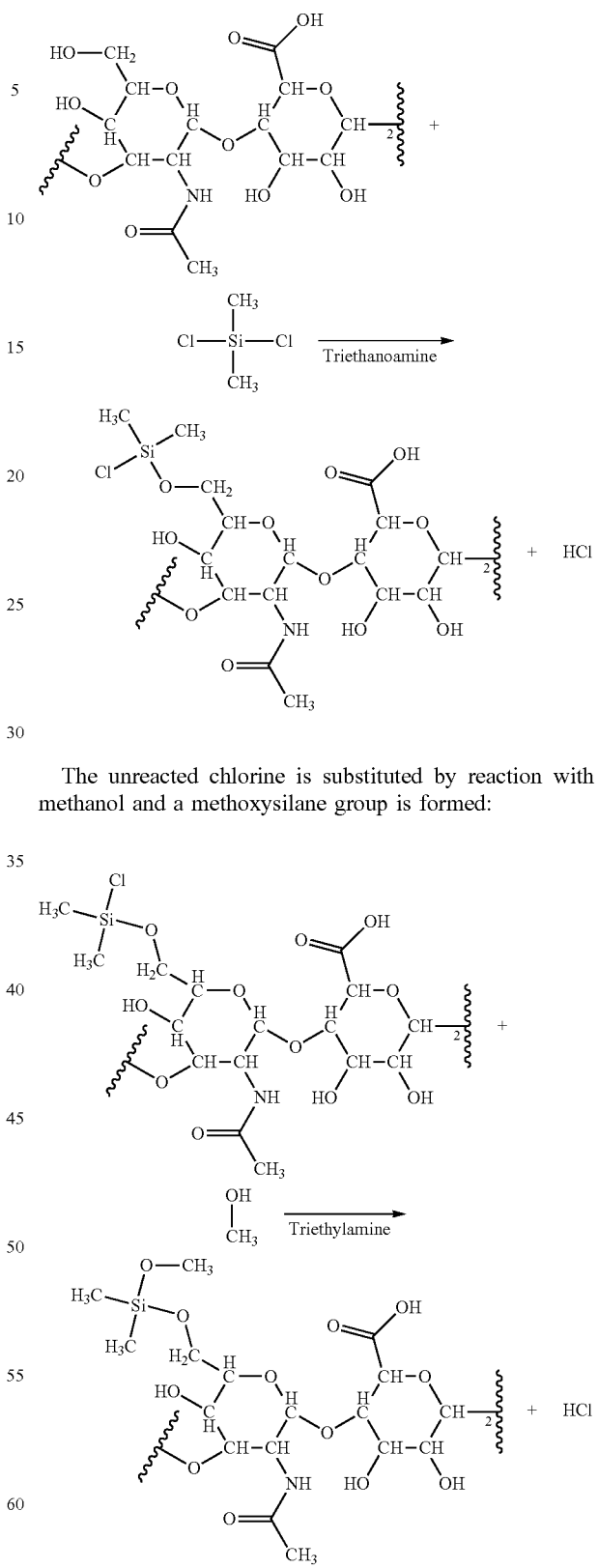

The unreacted chlorine is substituted by reaction with methanol and a methoxysilane group is formed:

The sodium that salifies the carboxyl group can thus be substituted by the triethylammonium formed during the reaction:

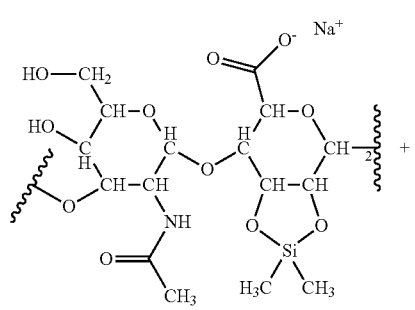

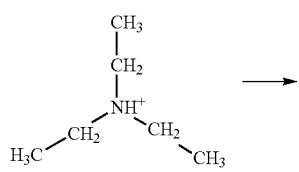

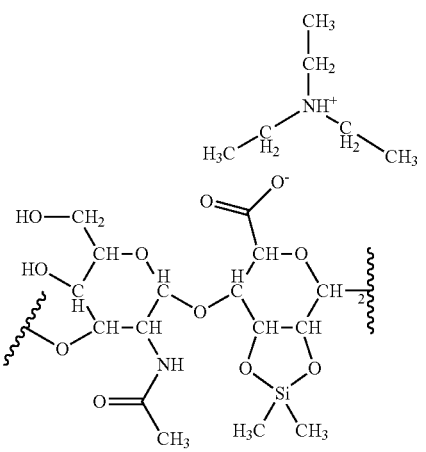

EXAMPLE 3

Silanization of Starch 1 g of starch in fine powder is suspended by stirring in 20 cc of n hexane. 5 ml of solution of n hexane containing 1 ml of dichlorodimethylsilane is added slowly.

It is kept under stirring for 15 minutes.

The solid is filtered and washed on a filter with n hexane until neutral reaction. Alternatively, it can be washed with ethanol until neutral pH. Subsequently, the product is vacuum dried at a temperature of 40° C.

EXAMPLE 4

Silanization of Starch in the Presence of a Base 4.4 ml of triethylamine is added under stirring to 80 ml of n hexane, followed by 1 g of starch in powder and 2 ml of $(CH_3)_2SiCl_2$ dissolved in 6 ml of n hexane. This is maintained under stirring for 2 hours, at 40° C. and then vacuum filtered and washed with hexane+1% of triethylamine, a mixture of methanol+10% of triethylamine is poured over the precipitate and maintained in contact for 10 minutes and then it is filtered and washed with hexane.

The triethylamine and its salt are removed completely or partly during washing with methanol and hexane.

The triethylamine that is not removed forms a molecular complex with the silanized starch by means of hydrogen bridges.

By changing the ratios between reagents, the reaction times and the temperature, it is possible to obtain a different degree of silanization.

The silyl-derivatives according to the invention, which are also indicated with the term SILHADE, which must not be intended to be in any manner limiting, are advantageously used in the cosmetic and/or pharmaceutical field.

For example, in the case of silyl-derivatives of hyaluronic acid, use in the cosmetic field makes it possible to achieve excellent results and an effect that is much longer lasting than that obtained with the same treatments carried out with hyaluronic acid alone.

Analogous results are obtained for use in the pharmaceutical field, for example to treat joint disorders, in the field of ophthalmology and/or otology.

The silyl-derivatives according to the invention can conveniently be formulated as active principles in suitable cosmetic and/or pharmaceutical compositions, as is and/or in the form of salts.

In particular, with regard to the salt forms of the derivatives according to the invention, a further aspect of the present invention is represented by the salts between the silyl-derivatives of formula (I and I') and amino acids and/or purine and pyrimidine bases. Said compounds, in appropriate conditions, can form salts with the silyl-derivatives of polysaccharides forming the subject-matter of the invention, according to the reaction schematized below:

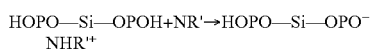

In this case HOPO—Si—OPOH (IV) represents a silyl-derivative of polysaccharide (or silanized polysaccharide) according to the invention, in which the hydroxyl of the acid group is highlighted and NR' is an amino acid or a nitrogenous base. It must be borne in mind that this further step to form salts with amino acids or nitrogenous bases involves the formation of an ionic and not a covalent bond.

In fact, for the purposes of the present invention, in an ionic bond the atoms are bound together by the attraction of oppositely charged ions while in a covalent bond the atoms are bound because they share electrons.

The amino acids and purine and pyrimidine bases can also form bonds with hydrogen bridges with the silanized polysaccharides.

By way of example, the scheme for obtaining a silanized heparin further salified with lysine (V) is indicated below.

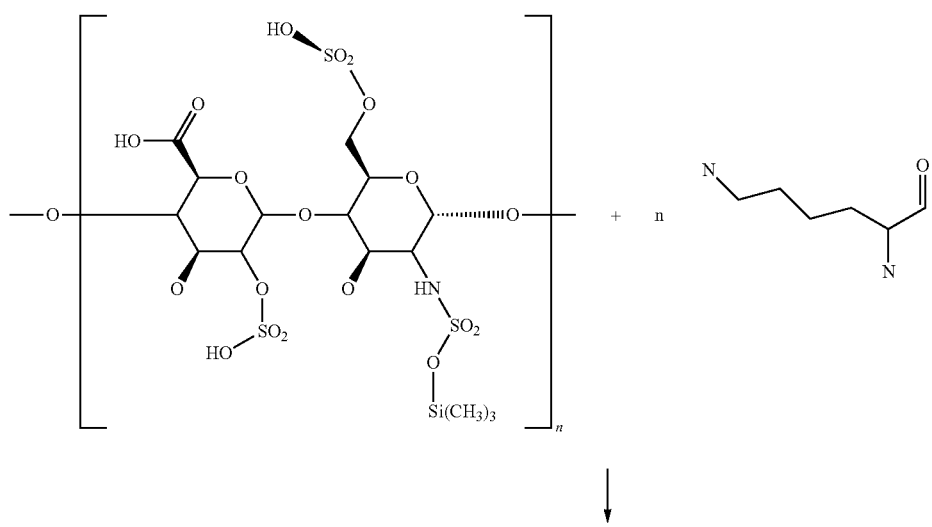
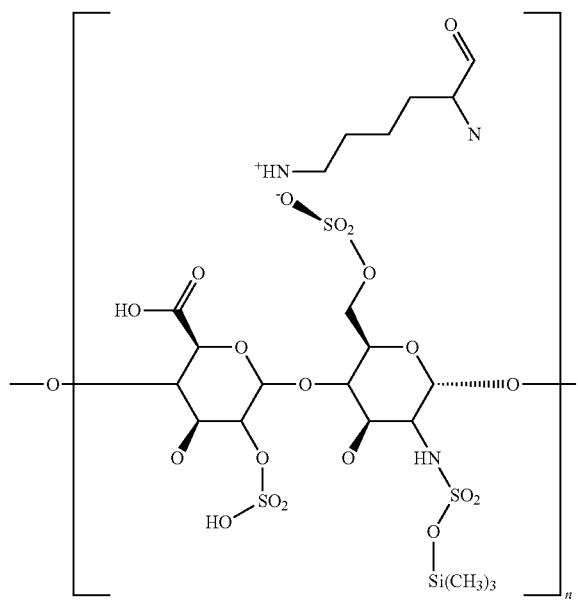
(V)

Instead, the following example shows the structure of the product (VI) obtained by a reaction between trimethylsilyl ether of hyaluronic acid and adenine.

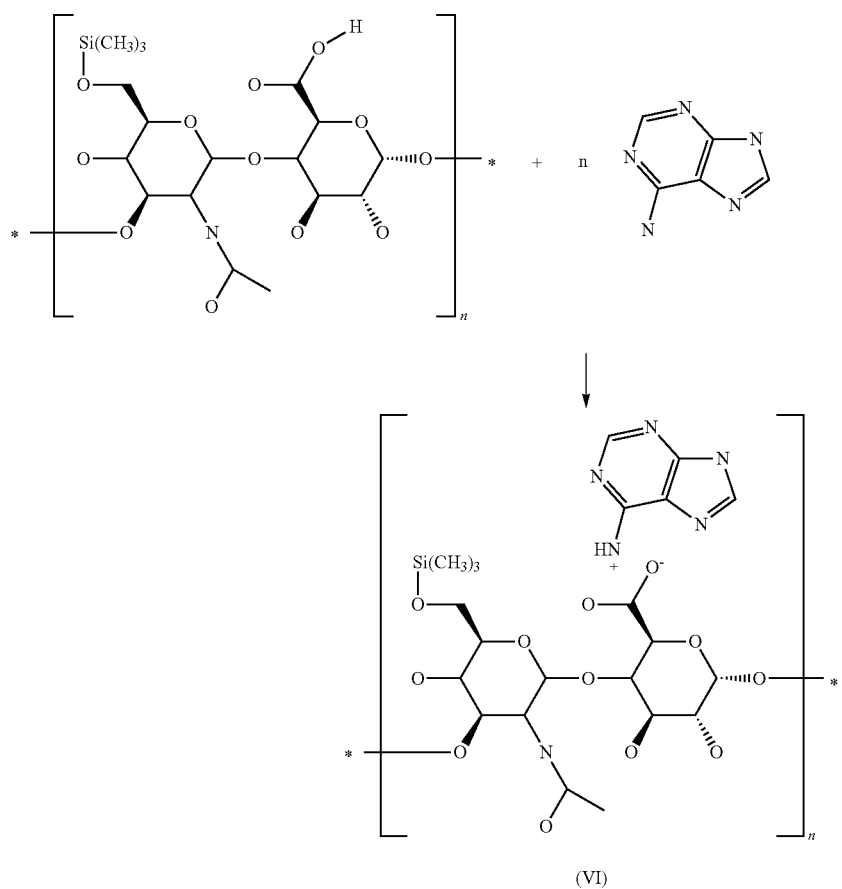

(VI)

The structure obtained by salification of the trimethylsilyldiether of the hyaluronic acid with thymine is shown:

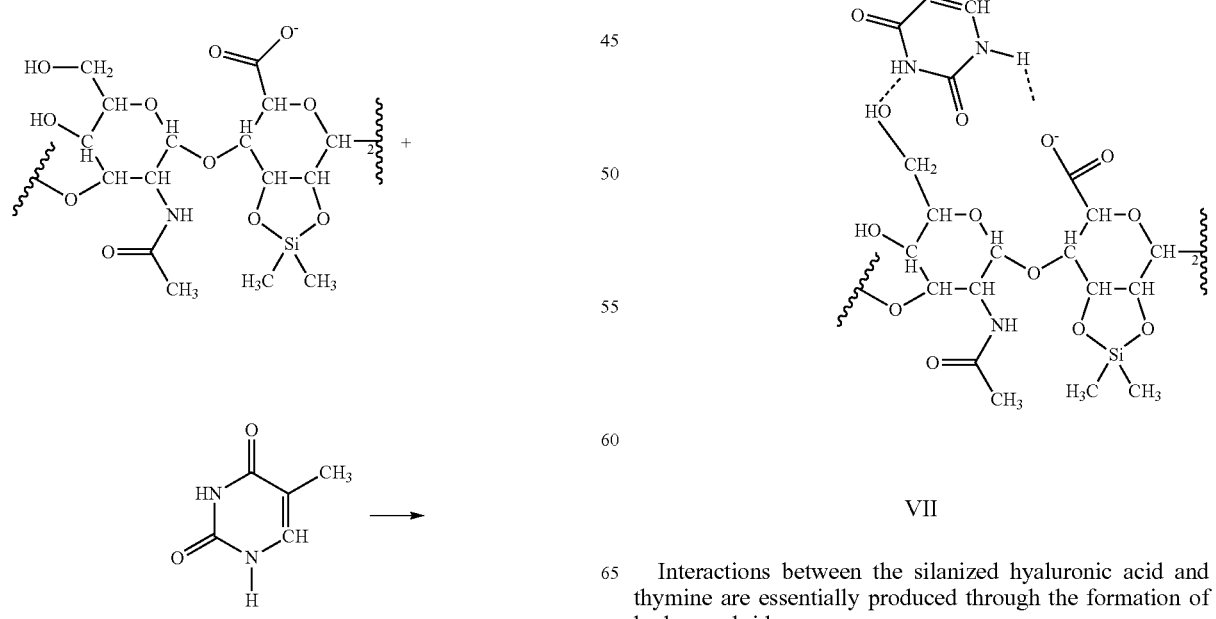

VII

Interactions between the silanized hyaluronic acid and thymine are essentially produced through the formation of hydrogen bridges.

Always according to the present invention, derivatives can also be obtained formed between the silyl of hyaluronic acid and several bases simultaneously. Again by way of example, the structure of the dimethyldisilyldiether of hyaluronic acid with adenine plus thymine is indicated.

In the example shown, each repeating unit is coordinated with a base, although derivatives in which not all the repeating units are occupied by a base can also be obtained.

The bases do not necessarily require to be used in a ratio of 1:1.

These variations allow modulation of the properties of the derivatives obtained according to the reactions described above, conducted at given predetermined conditions.

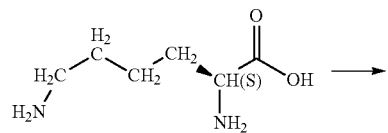

VIII

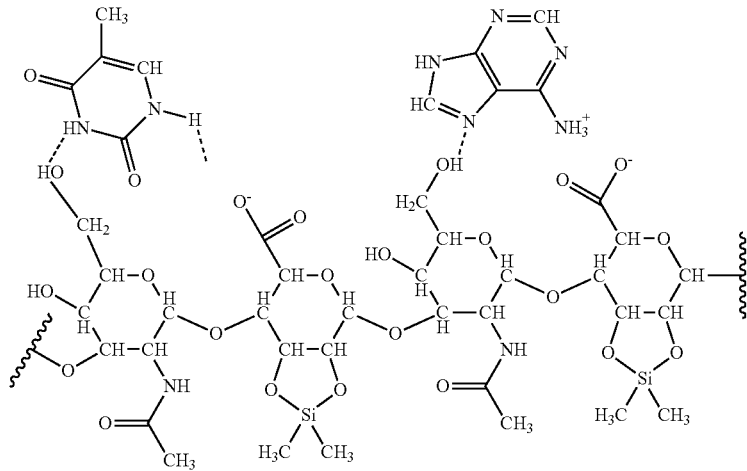

dimethyldisilyldiether of hyaluronic acid with adenine+ thymine.

Salification reaction of a silyl derivative of hyaluronic acid with lysine.

IX

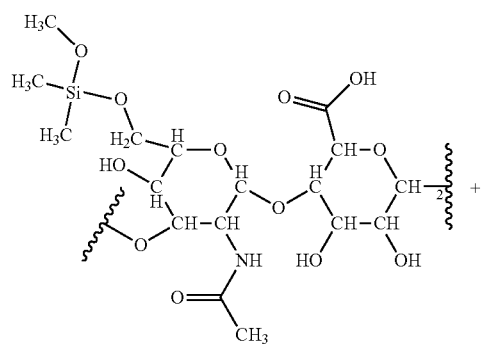

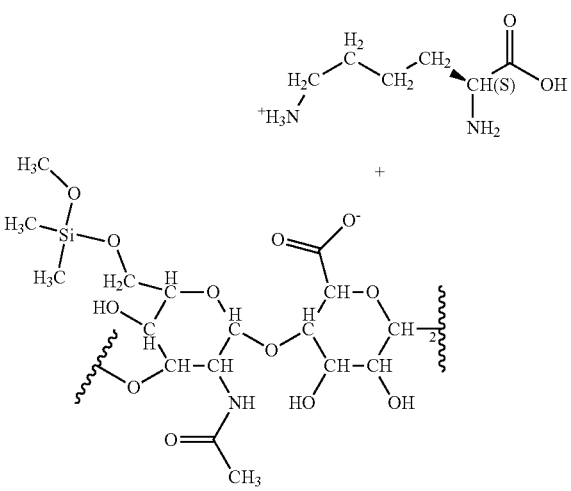

Dimethyl-Silylmethoxy-Silylether of Lysine Hyaluronate

Salification of the silyl derivative of hyaluronic acid with adenine and lysine is indicated by way of example. In the example, the silyl derivative of hyaluronic acid is salified with adenine and lysine in the lysine/adenine molar ratio=1:1.

5-hydroxymethyluracil
2-thiouracil
$N^4$-acetylcytosine
3-methylcytosine
5-methylcytosine
5-hydroxymethylcytosine
1-methyladenine
2-methyladenine

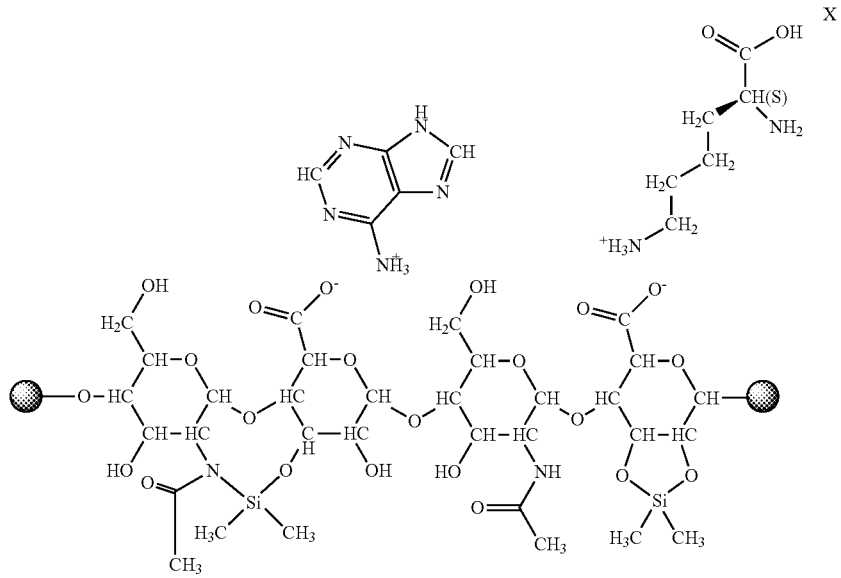

Always according to the invention, the amino acids and/or the nitrogenous bases that are used to obtain the salification products of the silyl-derivatives of polysaccharides according to the invention are selected from:

Amino Acids:
Alanine
Arginine
Aspargine
Aspartic acid
Cysteine
Phenylalanine
Glycine,
Glutamic acid
Isoleucine
Histidine
Leucine
Lysine
Methionine
Proline
Serine
Tyrosine
Threonine
Tryptophan
Valine
Polylysine Purine and Pyrimidine Bases:
Adenine
Guanine
Thymine
Cytosine
5,6-dihydrouracil
1-methyluracil
3-methyluracil 7-methyladenine
$N^6$-methyladenine
$N^6$, $N^6$-dimethyladenine
$N^6$-($\Delta^2$-isopentenyl)adenine
1-methylguanine
7-methylguanine
$N^2$-methylguanine
$N^2$, $N^2$-dimethylguanine

EXAMPLE 5

Reaction Between Adenine and Trimethylsilyl Ether of Hyaluronic Acid Obtaining Trimethylsilyl Ether Hyaluronate of Adenine (VI).

1 g of trimethylsilyl ether of sodium hyaluronate is reacted with 0.20 g of adenine hydrochloride hemihydrate.

Preparation of the Product Takes Place According to the Following Steps:
a) preparation of the adenine hydrochloride hemihydrate solution
b) addition of the trimethylsilyl ether of sodium hyaluronate
c) lyophilization of the product.

2 g of adenine is dissolved in 400 ml of deionized water. 10 g of trimethylsilyl ether of sodium hyaluronate is added slowly to the solution under stirring. Subsequently, the solution is maintained under stirring for approximately 1 hour to obtain complete homogenization of the product, then left to rest in a refrigerator at 5° C. for 12 hours, followed by lyophilization of the product.

EXAMPLE 6

Reaction Between Lysine and Trimethylsilyl Ether of Hyaluronic Acid Obtaining Trimethylsilyl Ether Hyaluronate of Lysine (IX)

1 g of trimethylsilyl ether of sodium hyaluronate is reacted with 0.4 g of lysine hydrochloride.

Preparation of the Product Takes Place According to the Following Steps:

d) preparation of the lysine hydrochloride solution
e) addition of trimethylsilyl ether of sodium hyaluronate
f) lyophilization of the product.

0.4 g of lysine hydrochloride is dissolved in 50 ml of deionized water.

1 g of trimethylsilyl ether of sodium hyaluronate is added slowly to the solution under stirring. Subsequently, the solution is maintained under stirring for approximately 1 hour to obtain complete homogenization of the product, then left to rest in a refrigerator at 5° C. for 12 hours, followed by lyophilization of the product.

EXAMPLE 7

Reaction Between Dimethylsilyldiether of Hyaluronic Acid with Adenine+Thymine (VIII)

1 g of dimethyldisilyldiether of hyaluronic acid is reacted with 0.15 g of adenine and 0.14 g of thymine.

Preparation of the Product Takes Place According to the Following Steps:

g) preparation of the adenine and thymine solution
h) addition of dimethyldisilyldiether of hyaluronic acid
i) lyophilization of the product.

0.15 g of adenine and 0.14 g of thymine are dissolved in 100 ml of deionized water.

1 g of dimethyldisilyldiether of hyaluronic acid is added slowly to the solution under stirring. Subsequently, the solution is maintained under stirring for approximately 1 hour to obtain complete homogenization of the product, then left to rest in a refrigerator at 5° C. for 12 hours, followed by lyophilization of the product.

As already stated, hyaluronic acid (HA) is notoriously used in the regeneration and repair of damaged tissue at various levels, both for its presence in the extracellular matrix, as fundamental constituent, and for the active role it takes in response to tissue damage.

In fact, in the inflammatory response phase to the damage, the matrix is rich in hyaluronic acid and fibrin, with intense migration of fibroblasts and endothelial cells to the wound area.

Hyaluronic acid allows for a biochemical environment that is favourable to cell migration and, with its action aimed at "capturing" free radicals and inhibiting the free circulation of proteins in the pericellular region, it performs a protective action against damages deriving from oxidative processes or enzymatic proteolysis, contributing to the phase of turning off the inflammatory process interacting with the cascade of anti-inflammatory cytokines.

Its role in physiological processes that lead to tissue regeneration derives from its hygroscopic, viscoelastic and angiomodulating properties, and from its ability to influence cell functions, due to the specific receptors on the cellular membrane.

The novel silyl-derivatives of hyaluronic acid, indicated above also with the acronym Silyl HA and with the term SILHADE, maintain the biological characteristics of hyaluronic acid and the effects thereof indicated above. However, their particular structure, the presence of particular substituents, specific chemical bonds and particular counterions, as well as their chemical-physical characteristics, produce a different and more powerful biological action with respect to that of hyaluronic acid as is or of its salts, in the examined diseases.

The derivatives according to the invention make it possible to achieve greater therapeutic efficacy and can be administered in various formulations, also in the form of complex salts, for example with amino acids and/or purines and pyrimidines.

Moreover, the SILHADE derivatives according to the invention can advantageously be used not only locally by topical application, but also orally, with consequent direct advantages in restoring the integrity of intestinal mucosa and its immunological and endocrine functions.

The novel derivatives according to the invention, enter the structure of the main macromolecules, such as elastin, collagen, proteoglycans and glycoproteins, promoting their regeneration.

They also perform a regulating action on metabolism and cell division, interacting with the extra and intracellular processes; they induce and modulate control and proliferation of fibroblasts (cells that produce collagen) at the level of connective tissue and produce positive regenerating effects in problems of skin aging. Moreover, they activate healing of trophic and vascular lesions, combating cellular aging with a trophic action exerted on the endothelium and on the walls of the vascular system. Always according to the invention, a further action performed by SILHADE silyl-derivatives is that of restoring elastin and collagen fibers.

They also function as metabolic protector, acting at various levels: they oppose lipid peroxidation, responsible for the release of free radicals and combat cross-linking and nonenzymatic glycosilation of the proteins forming the connective tissue, which causes rigidity and sclerosis, also exhibiting action as free radical scavengers.

The products of the invention regulate and stimulate fibroblast mitosis and, due to this property, play a role of fundamental importance in the dermal and epidermal cell regeneration process.

Moreover, the compounds of the invention promote healing of pressure sores and vascular or metabolic ulcers.

The keratinization process is correlated to the presence of S.O and of Hyaluronic acid.

The silyl-derivatives forming the subject-matter of the invention, also indicated with the term SILHADE, are particularly useful when used in the treatment of panniculopathy and in localized and generalized adiposity, both with formulations for vials and as dietary supplements administered orally.

The silyl-derivatives according to the invention are advantageously used in dermatological applications and in particular in the regeneration of impaired skin, acting on the stereo structure of the fundamental components; moreover, they induce significant improvement of cutaneous depressions, for example in the case of wrinkles and periocular and perilabial lines.

They delay and combat aging as a global phenomenon, inducing limitation of connective tissue degeneration and sclerosis and activation of microcirculation, and also opposing the formation of free radicals.

They have an ameliorative action on striae (especially if recent) and on scars and enhance dermal restoration and reorganization.

They also possess marked lipolytic properties.

This quality, combined with connective tissue regenerating activity and slowing of degradation of the collagen fibers positioned between adipocytes, makes the compounds according to the invention extremely efficacious in situations in which a component of tissue laxity and sclerosis coexists.

The compounds according to the invention also produce regenerating effects in pressure sores and activate healing of trophic and vascular lesions, and combat cellular aging with a trophic action on the endothelium and on the walls of the vascular system.

They also restore elastin and collagen fibers.

At pharmacological level, in the various formulations, the silyl-derivatives according to the present invention can be applied with topical, injectable, aerosol, oral formulations, all usable in the treatment of:

acne, cutaneous allergic conditions, arthritis and arthrosis, arteriosclerosis and vascular ulcers, burns, contusions, chilblains, gastrointestinal inflammatory diseases, edematous and sclerotic panniculopathy, vaginitis and vaginal mucositis, diabetes and diabetic foot, eczema, pressure sores, edema, hemorrhoids and proctitis, osteoporosis, inflammation of the gums, respiratory problems (asthma, COPD, acute bronchitis, recurrent bronchitis), psoriasis, sinusitis, digestive disorders caused by gastritis, duodenitis, ulcers, varices, cutaneous aging, mucositis following chemotherapy and radiotherapy, skin lesions following radiotherapy. They are also advantageously used as dietary supplement during chemotherapy and radiotherapy and during male and female infertility treatments.

The results of some studies relating to in-vitro experimentation on the modulation of the silanized derivatives according to the invention on inflammations and cytokine reactions are set forth below.

Objective of the study: silyl-derivatives according to the invention SILHADE and production of tFN and IL-1 in the inflammatory reaction.

An in-vitro study was carried out to evaluate the role of the silyl-derivatives of the invention in immunological response and in activation of the cytochemical cascade. The tests carried out on dendritic cells showed an increased stimulation thereof in determining activation of the receptors cd80, cd86 and cd86/ICAM 1 and therefore of triggering an immunological response.

In physiology, the inflammatory reaction is linked to specific and known stages that pass from recognition of the antigen or of the lesion damage and attempts to isolate the antigen and repair the lesion. This takes place with the specific cytochemical cascade, which determines the inflammatory environment of future evolution of the reaction.

Th1 and Th2 populations differ on the basis of the inflammatory stimuli and of the immunological reactions of individuals.

Lymphocyte populations that are involved in the maturation of dendritic cells (Th17 and Th22) have now been recognized.

The study of cytokines allows us to understand the method with which each person tends to fall ill and simultaneously allows us to understand the mechanism both of cell stimulation and of influencing the sol phase of the inflammatory reaction, in other words how the derivatives according to the invention cause an improved performance in the evolution of inflammation and how they influence transition from a sol phase to a gel phase, respecting times and without producing wild peptides or other waste products.

The experiments in progress are aimed at determining:
overview of the inflammatory and cytokine cascade in dermal and epidermal diseases and in chronic inflammatory diseases,
standardization of the immunological reaction and cell line involvement.
modification of the cytokine balance after contact with the silyl-derivatives of the invention both at the level of laboratory tests and at the level of clinical experimentation.

STUDY ON THE REGULATION OF INFLAMMATORY PROCESSES INVOLVED IN TISSUE REMODELLING AND WOUND HEALING.

Study of the effect of regulation of expression by monocytes/macrophages of metalloprotease such as collagenases, gelatinases, involved in tissue remodelling processes. The study was conducted on monocytes of peripheral blood compatibly with the toxicity results pursuant to point 1. The study consists of treating monocytes of peripheral blood with the silyl-derivatives of the invention (considering hyaluronic acid sodium salt (HA-Na) as control) alone or in combination with LPS as monocyte activator and quantifying the secretion of: MMP-1, MMP-2, MMP-9 and of the metalloproteinase inhibitor TIMP-1. These molecules perform an essential role in remodelling the extracellular matrix in inflammatory processes and in wound healing. Monocytes of peripheral blood are stimulated in vitro with LPS in the presence of silyl-derivative according to the invention or HA-Na as control and the secretion of metalloproteinases in the culture supernatants is quantified by ELISA.

Determining the influence of the derivatives according to the invention SILHADE on the polarization of T lymphocytes to specific functional phenotypes such as Th1, Th2, Th17. For this purpose naive $CD4^+$ T lymphocytes are polarized in vitro in the presence of controls or silyl-derivatives according to the invention. The functional phenotype of these lines is characterized by restimulation and intracytoplasmic staining to determine the production of IFN-g, IL-4, IL-17A, and to allow classification in the corresponding sub-populations Test on the Production of Fibroblasts and On Protein Synthesis Cell proliferation at different times through the MTT test: cell survival test after cycle synchronization with fibroblasts cultivated in adhesion to evaluate the cell proliferation potential induced by the tested product.

Increase of total proteins through the Bradford test: test to evaluate the total protein content in fibroblasts exposed to the product in question using scalar concentrations and different treatment times.

CONCLUSIONS

In fibroblasts treated with the sample corresponding to the silyl-derivatives according to the invention, in particular compounds pursuant to the structures (II), (III), (V), (VI), (VII), (VIII), (IX) and (X), there was an increase of proliferation (+40% maximum) and of protein synthesis (+18% maximum) with respect to untreated cells, in particular after 24 hours of exposure.

Therefore, the silyl-derivatives according to the invention exhibit the ability to stimulate both the proliferation and the increase of protein synthesis in characteristic cells forming the dermis and normally responsible for collagen and elastin synthesis.

The invention claimed is:

1. A silyl-derivative of a polysaccharide which is a derivatized polysaccharide (POH and/or PNH), with at least one silicon (Si) atom, said silicon atom deriving from at least one compound selected from a halogen silane, a halogen alkyl silane, a halogen aryl silane, a silane, an alkyl silane, a silanol, an aryl silane, an alkyl silanol, an aryl silanol, a silazane or a disilazane, characterized in that said polysaccharide is hyaluronic acid and said silyl-derivative has the formula (II)

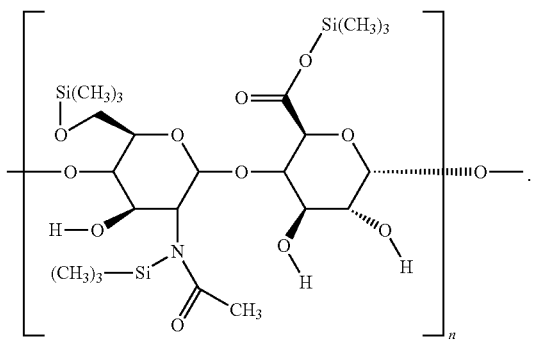

(II)

2. A salt between at least one silyl-derivative of a polysaccharide and at least one a pyrimidine base, characterized in that the salt is a salt between thymine and silanized hyaluronic acid of formula (VII),

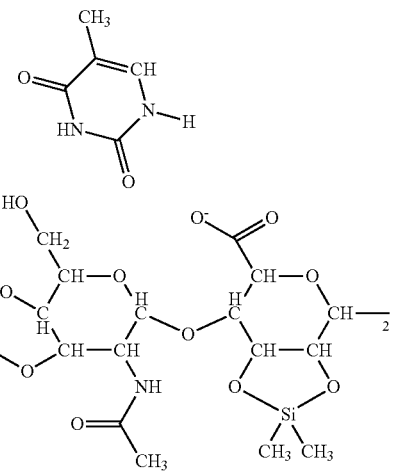

wherein said silicon atom is derived from at least one compound selected from a halogen silane, a halogen alkyl silane, a halogen aryl silane, a silane, an alkyl silane, a silanol, an aryl silane, an alkyl silanol, an aryl silanol, a silazane or a disilazane.

3. A salt between at least one silyl-derivative of a polysaccharide and at least one of a purine base and a pyrimidine base, characterized in that the salt is a mixed salt between thymine, adenine and silanized hyaluronic acid of formula (VIII),

VIII

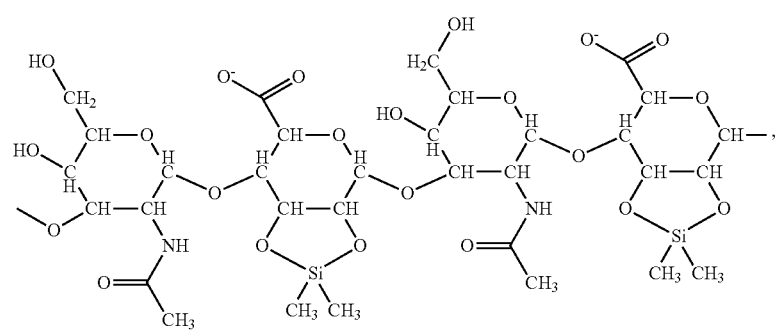

wherein said silicon atom is derived from at least one compound selected from a halogen silane, a halogen alkyl silane, a halogen aryl silane, a silane, an alkyl silane, a silanol, an aryl silane, an alkyl silanol, an aryl silanol, a silazane or a disilazane.

4. A salt between at least one silyl-derivative of a polysaccharide and at least an amino acid, characterized in that the salt is a salt between lysine and silanized hyaluronic acid of formula (IX)

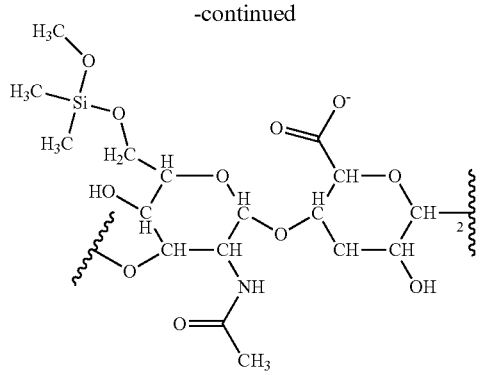

wherein said silicon atom deriving from at least one compound selected from a halogen silane, a halogen alkyl silane, a halogen aryl silane, a silane, an alkyl silane, a silanol, an aryl silane, an alkyl silanol, an aryl silanol, a silazane or a disilazane.

5. A salt between at least one silyl-derivative of a polysaccharide and at least one of an amino acid and a purine base, characterized in that the salt is a salt between lysine, adenine and silanized hyaluronic acid of formula (X)

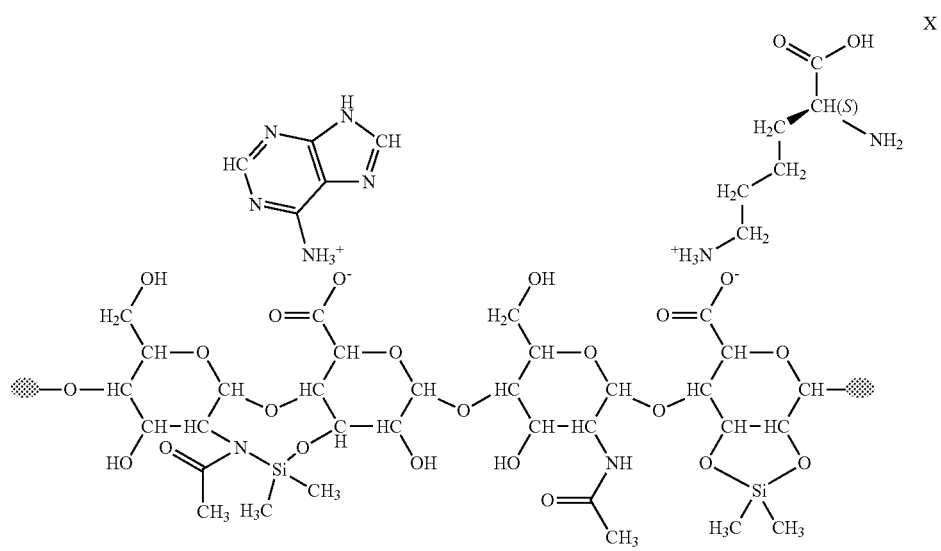

wherein said silicon atom is derived from at least one compound selected from a halogen silane, a halogen alkyl silane, a halogen aryl silane, an alkyl silane, a silanol, an aryl silane, an alkyl silanol, an aryl, a silazane or a disilazane.

* * * * *

UNITED STATES PATENT AND TRADEMARK OFFICE
CERTIFICATE OF CORRECTION

| | | |
|---|---|---|
| PATENT NO. | : 9,598,505 B2 | Page 1 of 1 |
| APPLICATION NO. | : 13/582750 | |
| DATED | : March 21, 2017 | |
| INVENTOR(S) | : Aita Gaspare et al. | |

It is certified that error appears in the above-identified patent and that said Letters Patent is hereby corrected as shown below:

On the Title Page

Item (73) the Assignee which appears as - SILDEHA SIXASS S.A. - should be changed to read -- SILDEHA SWISS S.A. --

Signed and Sealed this
Sixth Day of June, 2017

Michelle K. Lee
*Director of the United States Patent and Trademark Office*